(12) United States Patent
Bechtold et al.

(10) Patent No.: US 6,778,848 B1
(45) Date of Patent: Aug. 17, 2004

(54) DEVICE FOR THE ULTRASONIC THERAPY OF A FEMALE BREAST WITH PARALLEL SOUND DIRECTION

(75) Inventors: Mario Bechtold, Röttenbach (DE); Bernd Granz, Oberasbach (DE); Hans-Peter Heindel, Fürth (DE); Andrea Heilingbrunner, München (DE)

(73) Assignee: Siemens Aktiengesellschaft, Munich (DE)

( * ) Notice: Subject to any disclaimer, the term of this patent is extended or adjusted under 35 U.S.C. 154(b) by 716 days.

(21) Appl. No.: 09/179,357

(22) Filed: Oct. 14, 1998

(30) Foreign Application Priority Data

Oct. 14, 1997 (DE) ........................................ 197 45 400.3

(51) Int. Cl.[7] .............................. A61B 5/55; A61N 7/00
(52) U.S. Cl. .......................................... 600/411; 601/2
(58) Field of Search ................................ 600/411, 439, 600/459; 128/915; 601/2–4

(56) References Cited

U.S. PATENT DOCUMENTS 3,765,403 A  * 10/1973 Brenden ...................... 128/915
5,590,653 A  * 1/1997 Aida et al. .................... 600/411

FOREIGN PATENT DOCUMENTS

DE  195 21 475 A1  12/1996
EP   0 614 651 A1   9/1994

OTHER PUBLICATIONS

Sanghvi et al.: "New developments in Therapeutic Ultrasound", IEEE Engineering in Medicine and Biology, Nov./Dec. 1996, pp. 83–92.
Harvey E. Cline et al.: "Focused US System for MR Imaging–guided Tumor Ablation", Radiology Mar. 1995, pp. 731–737.
Hynynen et al.: "Tissue Thermometry during Ultrasound Exposure", Eur Urol 1993:23(suppl 1), pp. 12–16.
Richard S. Foster et al.: "High–Intensity Focused Ultrasound in the treatment of Prostatic Disease", Eur Urol 1993:23(suppl 1), pp. 29–33.

* cited by examiner

Primary Examiner—Ruth S. Smith
(74) Attorney, Agent, or Firm—Laurence A. Greenberg; Werner H. Stemer; Gregory L. Mayback

(57) ABSTRACT

A device provides ultrasonic therapy to a female breast. To this end, the breast is introduced into a container which, for a good acoustic coupling, is filled with at least one liquid. An ultrasonic transducer emits sound into the breast in a region which, in the positive and negative direction of rotation, related to the plane of the body of the female patient, covers angles of less than or equal to 50°. In a preferred embodiment, a compression pad and a fixing membrane are provided for fixing a position of the breast.

8 Claims, 1 Drawing Sheet

DEVICE FOR THE ULTRASONIC THERAPY OF A FEMALE BREAST WITH PARALLEL SOUND DIRECTION

BACKGROUND OF THE INVENTION

Field of the Invention

The invention relates to a device providing ultrasonic therapy to a female breast.

Major efforts have been made for the purpose of developing new noninvasive or minimally invasive methods of treatment of diseased, for example cancerous tissue. The advantage of such methods lies in a lower risk of complications during the treatment and in a more rapid healing process thereafter, since no open wounds need to heal. In this connection, the investigation and (further) development have also taken place of devices for ultrasonic thermotherapy in which diseased tissue is irradiated with focused high intensity ultrasound (high intensity focused ultrasound=HIFU) and the cancerous cells in the treatment area are destroyed by the resulting development of heat. With the HIFU method, it is possible, by reason of the focusing, to transport very high sound energies into a small target area having a diameter of, for example, a few millimeters. Within the focus region temperatures of 80° C. and above may be reached, while in contrast there are no substantial temperature rises in the surrounding tissue and also in the regions which the ultrasonic waves traverse on their path to the focus region. As a result, it is possible to reach and treat diseased tissue in the interior of the body, without injuring healthy tissue. A prerequisite for the method is, however, a sound path into the target area, which sound path is free from bones and/or air inclusions, since these obstruct the propagation of sound and thus make effective focusing impossible. Initial investigations in the laboratory and also in the clinic have been carried out on the human brain, the eye, the prostate and also the female breast.

The reference titled "Radiology", March 1995, pages 731 to 737, contains a description of a configuration for the ultrasonic therapy of a female breast, in the case of which configuration a sonic transducer irradiates the breast of a female patient, who is lying on her stomach, in an upward direction (perpendicular to the plane of the body of the female patient). The sonic transducer is situated in a water-filled container, which is sealed off with an interface foil. The female patient lies directly on the interface foil. In the article, no statement is made concerning the ultrasonic coupling between the interface foil and the breast. By way of example, it is possible to use for this purpose a coupling gel which is described, in the case of a comparable application of ultrasonic therapy for the treatment of prostate complaints, in "Eur Urol", 1993, Vol. 23 (supplement 1), pages 29 to 33. For the monitoring of the temperature progression during the treatment, the female patient is situated together with the configuration for ultrasonic therapy in an MR installation.

In the publication "Eur Urol", 1993, Vol. 23 (supplement 1), pages 12 to 16, there is described in-vivo-treatments of muscle and tumor tissue with focused high intensity ultrasound. The temperature in the treatment area is likewise monitored by MR diagnosis. However, the subject of the investigations is in this case is not the female breast but tissue of living rabbits. In this case also, the animals are situated directly over the ultrasonic transducer, so that they are struck frontally by the soundwaves which are emitted upwards.

In the case of the devices for ultrasonic therapy which are known in the mentioned prior art, irradiation with ultrasound takes place in each instance frontally to the plane of the body. In this case, no consideration is given to the fact that it is also possible for bones to be situated behind the tissue to be treated. Since, in comparison with soft muscle tissue or adipose tissue, bones have an acoustic absorption that is approximately up to 40 times greater. When using this configuration there is the danger that the bones will be destroyed or at least damaged, in the case of unintentional inaccurate focusing of the ultrasound, by reason of the intense heating.

SUMMARY OF THE INVENTION

It is accordingly an object of the invention to provide a device for the ultrasonic therapy of a female breast with parallel sound direction which overcomes the above-mentioned disadvantages of the prior art devices of this general type, which device, by suitable ultrasound guidance, eliminates the endangering of the bone system of the thorax, which bone system lies behind the breast, and at the same time provides good acoustic coupling.

With the foregoing and other objects in view there is provided, in accordance with the invention, a device for providing ultrasonic therapy to a breast of a female patient having a predetermined body plane, including: a container filled with at least one liquid for receiving a breast; and an ultrasonic transducer associated with the container, the ultrasonic transducer having a principal emission direction forming with a plane of a body of a female patient an angle of within minus 50° and plus 50°.

In this case, the invention is based on the finding that, compared with the ultrasonic diagnosis which has been known for a great length of time in ultrasonic therapy, by reason of the focused high intensity ultrasound which is employed, new and additional aspects have to be taken into consideration. It was recognized above all that the very greatly differing acoustic absorption coefficients of different parts of the human body play a decisive role. By way of example, one and the same acoustic intensity may lead to virtually no temperature increase in soft tissue and to intense heating and permanent damage in the bones, which absorb 40 times better. Specifically in the case of the therapy of the female breast, particular importance has to be ascribed to this aspect, since adjoining the soft breast tissue together with the thorax there is a body region which has a particularly high proportion of bone.

In the case of the ultrasonic therapy of a female breast, the device according to the invention excludes in a simple manner the endangering of the thorax bones, in that the sound is not irradiated perpendicularly, but preferably parallel to the body plane or at most within an angular range of ±50°, related to the body plane, into the breast. By reason of the claimed advantageous angular range for the sound emission, even where the treatment area is close to the thorax, there is no increased danger of damage to the bone or periosteum due to inaccurate focusing. On the other hand, even with the lateral emission method according to the invention, it is in principle possible for all regions of the breast to be covered and thus treated. As a result of the introduction, according to the invention, of the breast into a liquid, e.g. into water, a better acoustic coupling than with gel is achieved. Coupling with gel always involves the danger of air inclusions, in particular in the case of coupling surfaces which are as large as the female breast, and of changes due to drying out where the periods of treatment are relatively lengthy. Consequently, the device according to the invention offers advantages with respect to the safety of the female patient (bone damage) and to the effectiveness (acoustic coupling).

Accordingly, in an advantageous refinement the breast is mechanically fixed, so that the region to be treated cannot change in its local position in the course of the period of treatment. In a further advantageous embodiment, for this purpose an acoustically transmitting fixing membrane is inserted between the breast and the ultrasonic transducer. If at least a part of the breast is advantageously pressed against this acoustically transmitting fixing membrane, then the result is the positioning which is fixed during the period of treatment. For improved adaptation to the anatomical nature of the breast, the fixing membrane can be defined in a plurality of parts, or in arched fashion and/or to be elastic. Preferably, the pressure is exerted against the fixing membrane by compression pads that are provided in the container. In this case, the compression pads may be disposed in such a way that they fix the breast to the fixing membrane not only in the direction of action but also in other spatial directions, in particular in the two spatial directions perpendicular thereto.

In the case of the device according to the invention, the ultrasonic transducer and the breast can advantageously be placed in separate partial regions of the container or in two separate containers. In order to achieve a good acoustic coupling, the partial regions or the two containers are filled with a first and a second liquid, preferably with water, in particular with degassed and deionized water. For reasons of hygiene, it is advantageous if the ultrasonic transducer and the breast are not situated in the same liquid. To this end, it is possible to provide, for example, a liquid-impermeable but acoustically transmitting separating wall between the ultrasonic transducer and the breast.

In a further advantageous embodiment, at least the temperature is recorded on that side of the breast that faces away from the ultrasonic transducer. In addition, or instead, a recording of the acoustic power is also possible there. Further embodiments provide further sensors, which may be fitted at any desired advantageous positions in the container. In the case of ultrasonic therapy, decisive importance is prescribed to the matter of what proportion of the acoustic power has been absorbed in the breast tissue to be treated. From the two recorded measured variables temperature and acoustic intensity, it is possible to draw conclusions as to the acoustic power absorbed in the breast and as to further quantities derived therefrom, such as, for example, the degree of destruction of the diseased tissue. The more sensors installed, the more accurately these statements can be made.

A mechanical adjustment system of the ultrasonic transducer is advantageously configured in two parts. The ultrasonic transducer can in the first instance be manually prepositioned and subsequently repositioned or finely positioned electrically, preferably by a hydraulic drive. The two-stage procedure permits a limitation of the expenditure that must be implemented for the hydraulic drive. Drives become all the more cost intensive the greater their region of adjustment. By the manual prepositioning, the ultrasonic transducer is already aligned in coarse terms onto the target area. In order to direct the focus precisely onto the diseased tissue, it is then only necessary for the hydraulic drive to carry out minor changes of position. Thus, the hydraulic drive manages with small ranges of adjustment, and can accordingly be configured economically. Also, the hydraulic drive can be configured for automatically positioning the ultrasonic transducer.

If the ultrasonic transducer is advantageously configured as a 2D (two-dimensional) array, the positioning of the focus of which may be electronically controlled in all three spatial directions, it is possible to dispense entirely with the electrohydraulic fine positioning. In this case, the mechanical adjustment system is accordingly only single-stage. It then includes merely the manual prepositioning. In an advantageous embodiment, the electronically controlled focus of the 2D array may be positioned in the entire breast region, without any need to undertake a mechanical change of position of the array. In this case, it is possible to dispense with a separate mechanical adjustment system.

As an advantageous variant refinement, the device according to the invention for ultrasonic therapy is used together with an MR diagnosis. With the aid of the data obtained from the MR-based temperature monitoring, the various setting variables of the device for ultrasonic therapy, such as for example sound direction and sound focusing, focus position and focus magnitude as well as the acoustic intensity, can be readjusted.

Other features which are considered as characteristic for the invention are set forth in the appended claims.

Although the invention is illustrated and described herein as embodied in a device for the ultrasonic therapy of a female breast with parallel sound direction, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
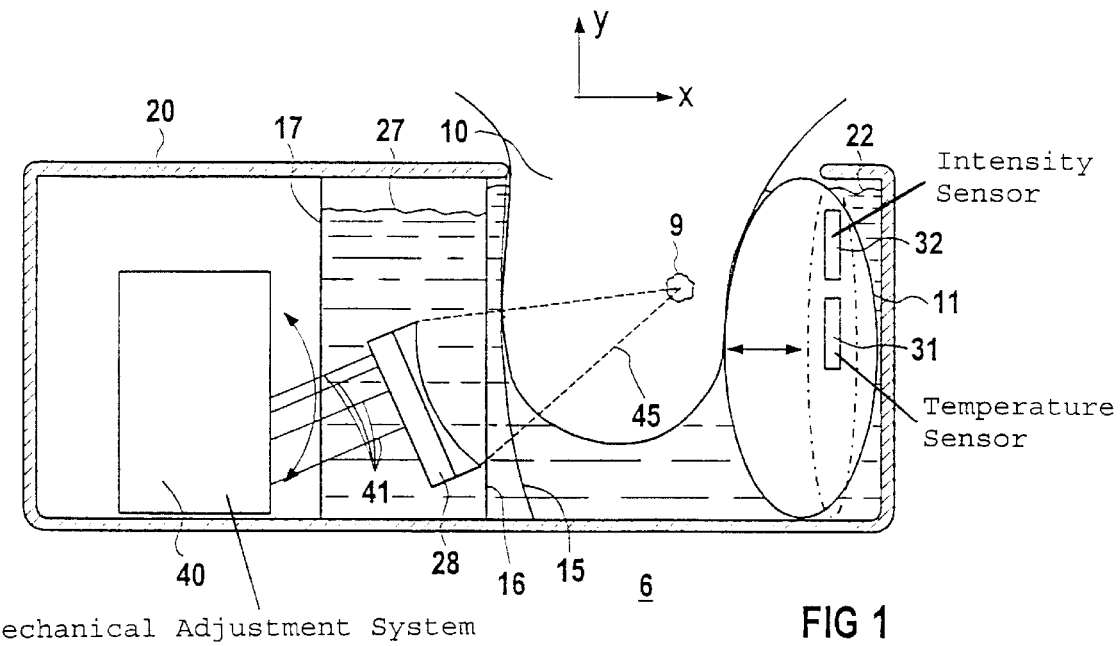
FIG. 1 is a diagrammatic view of a central cross section of a device for ultrasonic therapy of a female breast according to the invention.

In all the figures of the drawing, sub-features and integral parts which correspond to one another bear the same reference symbol in each case. Referring now to the figures of the drawing in detail and first, particularly, to FIG. 1 thereof, there is shown an ultrasonic therapy device 6 for a female breast 10 represented in the form of a central cross section.

Figure 2:
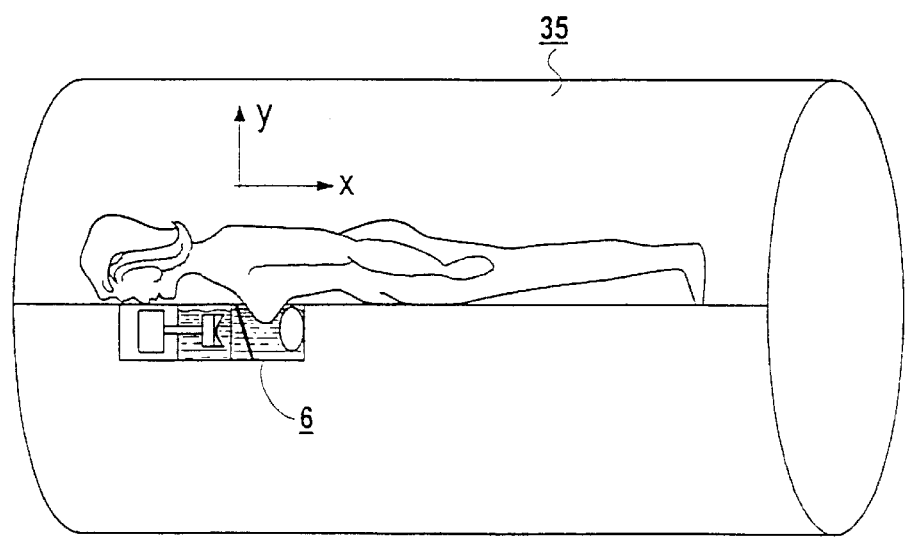
FIG. 2 is a diagrammatic view of the device for ultrasonic therapy as a component part of an MR installation.

The ultrasonic therapy device 6 includes a container 20, into which the breast 10 can be introduced, and an ultrasonic transducer 28. The emission direction of the ultrasonic transducer 28 can be altered, so that the focus of emitted sound waves 45 onto a tissue region 9 to be treated can be set with any desired position in the breast 10. To illustrate the orientations, a coordinate system with auxiliary axes X and Y is indicated in FIGS. 1 and 2. The ultrasonic transducer 28 treats the breast 10 with ultrasound substantially parallel to an orientation within the plane of the body of the female patient, which is defined in FIG. 1 by the auxiliary axis X. The mechanical adjustment region of the ultrasonic transducer 28 is dimensioned in such a way that the emission of sound can take place within an angular range between minus 50° and plus 50°, related to the auxiliary axis X.

The breast 10 is pressed by a compression pad 11 against a fixing membrane 15 and thus fixed at least in the direction of the auxiliary axis X. The breast 10 can, if required, be fixed by further compression pads (not shown) in the direction of the auxiliary axis Y and also in further directions. Accordingly, the breast 10 always remains in the same position in the course of the ultrasonic treatment. In this case, the acoustically transmitting fixing membrane 15 serves at the same time as an access window for the ultrasonic waves to be injected. The compression pad 11 is preferably filled with water and can be altered in its volume by a variation of the filling quantity. In order to achieve the greatest possible comfort on contact, the compression pad 11 is produced from a material compatible with skin, in the present illustrative embodiment from latex.

A temperature sensor 31 and an acoustic intensity sensor 32 are fitted in the compression pad 11. With the aid of the recorded temperature and acoustic intensity, conclusions are drawn as to the acoustic power absorbed in the breast 10 and as to further derived quantities such as, for example, the tissue destruction.

The ultrasonic transducer 28 is situated in a second partial region of the container 20, which is connected via an acoustically transmitting first separating wall 16 to the first partial region of the container 20, into which the breast is introduced during the treatment. The first separating wall 16 is constructed to be impermeable to liquid. In order to achieve a good acoustic coupling, a first partial region of the container 20 is filled with a liquid 22, in the present case with degassed and deionized water. A second partial region of the container 20 is filled with a second liquid 27, likewise with degassed and deionized water. In this case, the first separating wall 16, which is impermeable to liquid, prevents an intermixing of the two liquids 22 and 27 and is desirable for reasons of hygiene. The first separating wall 16 consists of a Mylar foil having a thickness of 75 μm. The fixing membrane 15 is constructed as a perforated foil, likewise of Mylar. The first separating wall 16 and also the fixing membrane 15 are acoustically transmitting and do not influence the focusing of the ultrasonic beam. The soundwaves 45 emitted by the ultrasonic transducer 28 with focusing onto the diseased tissue region 9 are not influenced, or are only slightly influenced, on passing through the first separating wall 16 and the fixing membrane 15.

To align the ultrasonic emission onto the diseased tissue region, a mechanical adjustment system 40 for the ultrasonic transducer 28 is accommodated in a third partial region of the container 20. The mechanical adjustment system 40 contains devices for both manual and also for electrohydraulic alteration of the position of the ultrasonic transducer 28. The coarse positioning or prepositioning takes place by hand, and the fine positioning by an electrical hydraulic drive. In this case, adjustment shafts 41 provide the force transmission between mechanical adjustment system 40 and ultrasonic transducer 28. The third partial region of the container 20 is separated from the second by a second separating wall 17, which is impermeable to liquid and which is made of latex.

In the illustrative embodiment of FIG. 2, the ultrasonic therapy device 6 is a component part of an MR installation 35 and is operated in conjunction with the latter. In the case of the ultrasonic therapy of diseased breast tissue, MR diagnosis represents a preferred method for monitoring the temperatures in a treated tissue region.

We claim:

1. A device for providing ultrasonic therapy to a breast of a patient, comprising:

a container filled with at least one liquid for receiving a breast of a patient;

an acoustically transmitting fixing membrane disposed in said container for mechanically fixing the breast of the patient; and an ultrasonic transducer associated with said container, said ultrasonic transducer emitting sound waves having a principal emission direction forming with a plane of a body of the patient an angle of less than or equal to 50°, said emission direction to be altered for setting the focus of said sound waves to any tissue region within the breast of the patient.

2. The device according to claim 1, wherein the breast and said ultrasonic transducer are spatially separated from one another at least by said acoustically transmitting fixing membrane.

3. The device according to claim 2, including a compression pad for pressing at least a part of the breast against said acoustically transmitting fixing membrane.

4. The device according claim 1, including a first separating wall having good acoustically transmitting properties and being impermeable to liquid, said first separating wall disposed in said container for keeping the at least one liquid away from said ultrasonic transducer.

5. The device according claim 1, including at least one sensor disposed at least on a side of the breast facing away from said ultrasonic transducer, said at least one sensor measuring at least one of temperature and acoustic power.

6. The device according to claim 1, including a positioning device for manually positioning said ultrasonic transducer.

7. The device according to claim 6, including a hydraulic drive for automatically positioning said ultrasonic transducer.

8. A device for providing ultrasonic therapy to a breast of a patient, comprising:

a magnetic resonance device;

a container filled with at least one liquid for receiving a breast of a patient disposed in said magnetic resonance device;

an acoustically transmitting fixing membrane disposed in said container for mechanically fixing the breast of the patient; and an ultrasonic transducer associated with said container, said ultrasonic transducer emitting sound waves having a principal emission direction forming with a plane of a body of the patient an angle of less than or equal to 50°, said emission direction to be altered for setting the focus of said sound waves to any tissue region within the breast of the patient.

* * * * *